(12) United States Patent
Kuczynski et al.

(10) Patent No.: US 10,107,541 B2
(45) Date of Patent: Oct. 23, 2018

(54) REUSABLE COLD PACK

(71) Applicant: International Business Machines Corporation, Armonk, NY (US)

(72) Inventors: Joseph Kuczynski, North Port, FL (US); Marvin M. Misgen, Rochester, MN (US); Debra Neuman-Horn, Rochester, MN (US); Joseph F. Prisco, Rochester, MN (US); Kevin J. Przybylski, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 13 days.

(21) Appl. No.: 15/351,150

(22) Filed: Nov. 14, 2016

(65) Prior Publication Data
US 2018/0135905 A1  May 17, 2018

(51) Int. Cl.
*F25D 5/00* (2006.01)
*F25D 5/02* (2006.01)

(52) U.S. Cl.
CPC ..................................... *F25D 5/02* (2013.01)

(58) Field of Classification Search
CPC . F25D 5/00; F25D 5/02; F25D 31/007; F25D 2332/805; A47J 36/28; B65D 81/3484
See application file for complete search history.

(56) References Cited

U.S. PATENT DOCUMENTS

| | | | | |
|---|---|---|---|---|
| 4,462,224 A | * | 7/1984 | Dunshee | A61F 7/106 206/219 |
| 4,780,117 A | * | 10/1988 | Lahey | A61F 7/106 126/263.07 |
| 4,886,063 A | * | 12/1989 | Crews | A61F 7/02 607/112 |
| 4,967,573 A | * | 11/1990 | Wilhelm | A61F 7/106 607/114 |
| 5,190,033 A | | 3/1993 | Johnson | |
| 5,423,996 A | | 6/1995 | Salyer | |
| 5,534,020 A | * | 7/1996 | Cheney, III | A61F 7/03 126/204 |
| 5,545,197 A | * | 8/1996 | Bowen | A61F 7/03 126/204 |
| 5,785,980 A | * | 7/1998 | Mathewson | A41D 20/005 424/402 |

(Continued)

FOREIGN PATENT DOCUMENTS

KR    1020050067393 A    7/2005

*Primary Examiner* — Kun Kai Ma
(74) *Attorney, Agent, or Firm* — Patterson + Sheridan, LLP

(57) ABSTRACT

Embodiments described herein relate to a reusable chemical cold pack. The apparatus includes a body which defines a chamber having two volumes separated by a thin film composite membrane. The thin film composite membrane includes a fabric material sheet, a thermoplastic polymer material sheet, and a polyamide material sheet. A first volume disposed on one side of the thin film composite membrane contains a solvent and a second volume disposed on an opposite side of the thin film composite membrane contains a solute. A check valve is disposed through the thin film composite membrane and enables mixing of the solvent and the solute. The solvent and the solute may also be separated after mixing by diffusion of the solvent through the thin film composite membrane.

19 Claims, 2 Drawing Sheets

(56) References Cited

U.S. PATENT DOCUMENTS

| | | | | |
|---|---|---|---|---|
| 5,843,145 A | * | 12/1998 | Brink | A61F 7/02 607/108 |
| 6,182,850 B1 | * | 2/2001 | Marbler | B65D 77/225 220/359.3 |
| 6,935,492 B1 | * | 8/2005 | Loeb | B65D 81/3272 206/219 |
| 2001/0008072 A1 | * | 7/2001 | Kohout | A61F 7/106 62/4 |
| 2004/0181156 A1 | | 9/2004 | Kingsford et al. | |
| 2004/0186541 A1 | * | 9/2004 | Agarwal | A61F 7/03 607/114 |
| 2006/0201187 A1 | * | 9/2006 | Smolko | A41D 13/0053 62/315 |
| 2008/0005846 A1 | * | 1/2008 | Liao | B65D 81/052 5/713 |
| 2008/0141683 A1 | * | 6/2008 | O'Connor | A61F 7/106 62/4 |
| 2008/0173670 A1 | * | 7/2008 | Macler | B65B 69/0041 222/81 |
| 2009/0198311 A1 | * | 8/2009 | Johnson | A61F 7/106 607/109 |
| 2010/0125317 A1 | * | 5/2010 | Lu | A61F 7/10 607/104 |
| 2013/0174581 A1 | | 7/2013 | Rasmussen et al. | |
| 2015/0253057 A1 | * | 9/2015 | Leavitt | C09K 5/066 62/4 |
| 2016/0058218 A1 | * | 3/2016 | Yoshifusa | A47G 9/1027 428/12 |

* cited by examiner

REUSABLE COLD PACK

BACKGROUND

Field

Embodiments of the present disclosure generally relate to chemical cold packs. More specifically, embodiments described herein relate to a reusable chemical cold pack.

Description of the Related Art

Ice packs are useful tools commonly utilized to relieve pain, swelling, and inflammation from injuries and other conditions, such as arthritis or the like. Conventional cold packs are available in a variety of form factors, including chemical cold packs. Chemical cold packs utilize endothermic reaction characteristics of a chemical mixture to provide the cooling effects commonly associated with cold packs. The chemicals are generally separated from one another until the cold pack is utilized. In operation, conventional chemical cold packs require a user to break an inner seal which allows the mixing of the chemicals to facilitate the ensuing endothermic reaction. Once the chemicals have been mixed and the reaction has reached equilibrium, the cold packs are spent and may be discarded because there is no way to reuse the cold pack.

While conventional cold packs have improved cold pack accessibility and availability when refrigeration is not accessible, barriers to cold pack utilization still exist. For example, remote cold pack utilization for extended durations, such as a hiking expedition, a user would likely pack multiple conventional cold packs because of the one-time use inherent to the endothermic reaction. Transporting multiple chemical cold packs may be undesirable when factoring weight and space during such journeys. Moreover, single use chemical cold packs are environmentally taxing as the packs are worthless after utilization and will be thrown in the garbage.

Thus, what is needed in the art are improved cold packs.

SUMMARY

In one embodiment, a cold pack apparatus is provided. The apparatus includes a body defining an enclosure and the body at least partially defines a first volume and a second volume. A thin film composite membrane is coupled to the body between the first volume and the second volume and a check valve is disposed within the thin film composite membrane. The check valve is also in fluid communication with the first volume and the second volume.

In another embodiment, a cold pack apparatus is provided. The apparatus includes a body defining a chamber therein and a fabric material sheet is coupled to the body to define a first volume and a second volume within the chamber. A thermoplastic polymer material sheet is coupled to the fabric material sheet and the body and a polyamide material sheet is coupled to the thermoplastic polymer material sheet and the body. A check valve is disposed through the fabric material sheet, the thermoplastic polymer material sheet, and the polyamide material sheet. The check valve is also in fluid communication with the first volume and the second volume.

In yet another embodiment, a cold pack apparatus is provided. The apparatus includes a body defining a chamber therein and the body at least partially defines a first volume and a second volume within the chamber. A thin film composite membrane is coupled to the body between the first volume and the second volume, a check valve is disposed within the thin film composite membrane, and the check valve is in fluid communication with the first volume and the second volume. A fluid inlet port is disposed in the body in fluid communication with the first volume and a fluid outlet port is disposed in the body in fluid communication with the second volume.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, may admit to other equally effective embodiments.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

Embodiments described herein relate to a reusable chemical cold pack. The apparatus includes a body which defines a chamber having two volumes separated by a thin film composite membrane. The thin film composite membrane includes a fabric material sheet, a thermoplastic polymer material sheet, and a polyamide material sheet. A first volume disposed on one side of the thin film composite membrane contains a solvent and a second volume disposed on an opposite side of the thin film composite membrane contains a solute. A check valve is disposed through the thin film composite membrane and enables mixing of the solvent and the solute. The solvent and the solute may also be separated after mixing by diffusion of the solvent through the thin film composite membrane.

Figure 1:
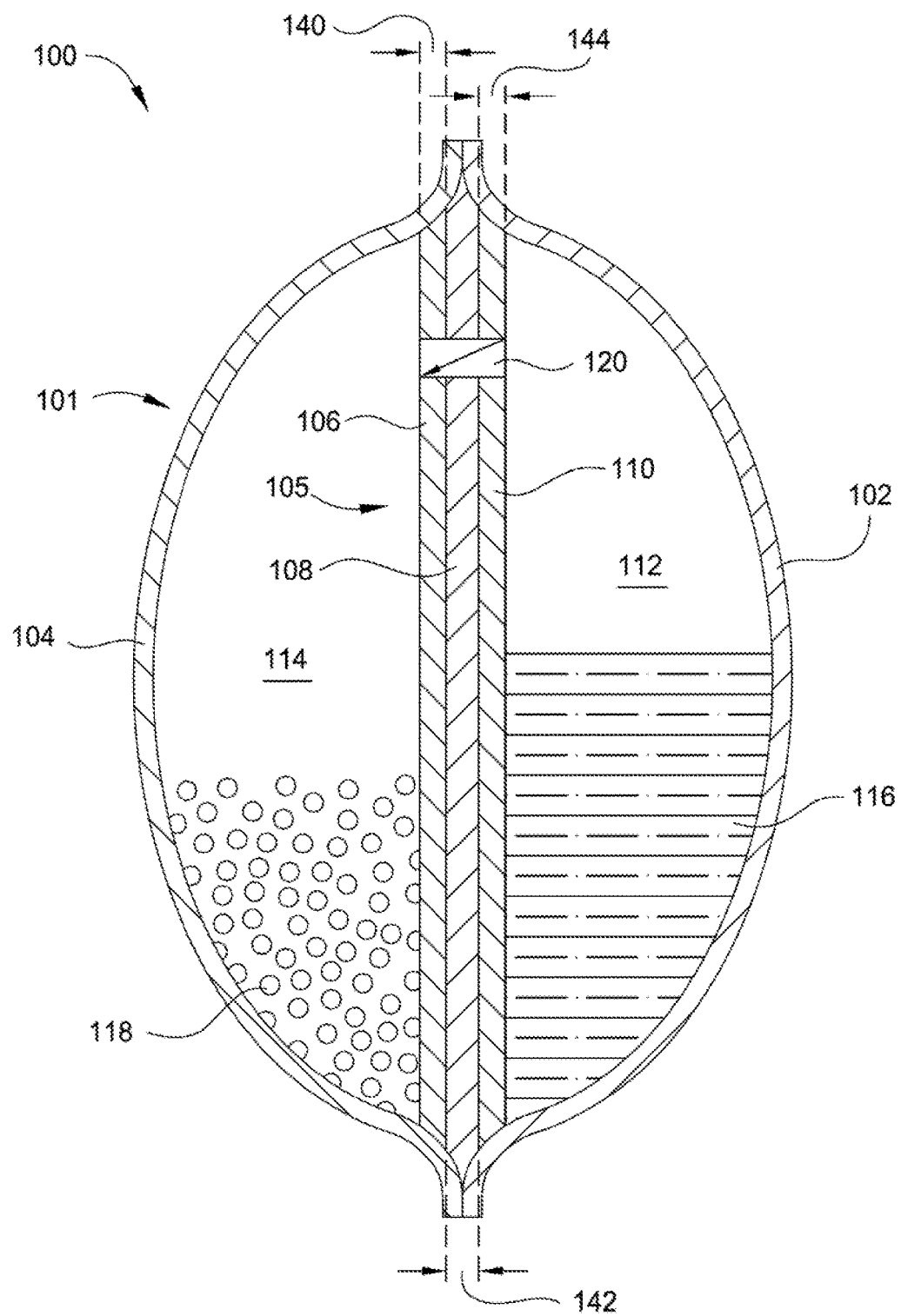
FIG. 1 illustrates a schematic, cross-sectional view of a cold pack according to one embodiment described herein.

FIG. 1 illustrates a schematic, cross-sectional view of a cold pack 100 according to one embodiment described herein. The cold pack 100 includes a body 101 which defines a chamber or enclosure therein, a thin film composite (TFC) membrane 105 disposed within the chamber and coupled to the body 101, and a check valve 120 disposed within the TFC membrane 105. The body 101 includes a first body member 102 and a second body member 104. The body members 102, 104 comprise the body 101 and the first body member 102 and second body member 104 are coupled to one another at distal regions of the body 101. For example, the first and second body members 102, 104 may be plastic welded, glued, stitched or otherwise adhered to one another to form a chamber within the body 101. The bond between the body members 102, 104 is of sufficient strength and structural integrity to withstand pressure or compressive force applied on the body 101 without breaking. For example, the body members 102, 104 are adhered in a manner that remains bonded upon application of a force sufficient to move a liquid across the TFC membrane 105.

In one embodiment, the body members 102, 104 are formed from a compliant or flexible material to enable the cold pack 100 to mold or form to a user's appendage or other body part where cooling therapy is desirable. For example, the body members 102, 104 may be formed from a plastic material, a polymer material, or a thermoplastic material. In one embodiment, the body members 102, 104 are formed from a polypropylene material, a polyethylene material, or a combination thereof. In another embodiment, the body members 102, 104 are formed from an ethylene propylene diene polymer (EPDM) rubber compound. In another embodiment, the body members 102, 104 may also be aluminized or otherwise coated on interior or exterior surfaces with liquid impermeable materials. Similarly, the body members 102, 104 may have a metallized coating disposed thereon to prevent diffusion of liquids and gases (i.e. oxygen) therethrough.

The TFC membrane 105 is coupled to the body 101 within the chamber in an orientation that divides the chamber into a first volume 112 and a second volume 114. Generally, the first volume 112 and the second volume 114 are disposed on opposing sides of the TFC membrane 105. In one embodiment, the TFC membrane 105 is coupled to the first body member 102 and the second body member 104 at the distal regions of the body 101 where the first and second body members 102, 104 are coupled together. The TFC membrane 105 divides the chamber defined by the body 101 into at least two separate volumes (i.e. the first and second volumes 112, 114) to create separate environments within the body 101.

The TFC membrane 105 includes a first material layer 106, a second material layer 108, and a third material layer 110. In one embodiment, the first material layer 106 is a fabric material sheet. In another embodiment, the first material layer 106 is a non-woven fabric material. In this embodiment, the non-woven fabric is a material which is formed by bonding or entangling fibers or filaments of a desired material. For example, the non-woven fabric may be formed from a polymer material by various manufacturing processes, such as a spunlaid process, a flashspun process, a staple process, or the like. The first material layer 106 is selected to be permeable to a liquid, such as water or other solvent liquids.

A thickness 140 of the first material layer 106 is between about 50 μm and about 200 μm, such as between about 100 μm and about 140 μm, for example, about 120 μm. As illustrated, the first material layer 106 is disposed adjacent the second volume 114. Alternatively, the first material layer 106 is disposed adjacent the first volume 112. In both embodiments, the first material layer 106 is disposed adjacent the volume which contains a solute.

The second material layer 108 is disposed on the first material layer 106. In one embodiment, the second material layer 108 is a thermoplastic polymer material sheet. For example, the second material layer 108 may be formed from a polysulfone or polyethersulfone material. In this embodiment, the second material layer 108 is microporous such that the second material layer is permeable to a liquid solvent. A thickness 142 of the second material layer 108 is between about 20 μm and about 80 μm, such as about 40 μm.

The third material layer 110 is disposed on the second material layer 108. In one embodiment, the first material layer 106 and the third material layer 110 sandwich the second material layer 108. The first material layer 106 and the second material layer 108 are generally porous and permeable to a selected solvent and provide structural integrity to the TFC membrane 105. As illustrated, the third material layer 110 is disposed adjacent the first volume 112. Alternatively, the third material layer 110 is disposed adjacent the second volume 114. In both embodiments, the third material layer is disposed adjacent the volume which contains a solvent. In one embodiment, the third material layer 110 is a polyamide material sheet. The third material layer 110 may have a thickness 144 of less than about 400 nm, such as less than about 200 nm.

The third material layer 110 is selectively permeable to one or more types of material. For example, the third material layer is permeable to one or more liquid solvents while being impermeable or relatively impermeable to salts having ionic radii greater than a pore size associated with the polyamide material. In one example, the third material layer 110 is selected to reject passage of salt ions from the second volume 114 to the first volume 112.

The TFC membrane 105 also has a check valve 120 disposed therein. The check valve 120 extends through the TFC membrane 105 such that the check valve 120 is in fluid communication with both the first volume 112 and the second volume 114. In one embodiment, the check valve 120 is a one way check valve which permits the passage of fluid from the first volume 112 to the second volume 114 but prevents passage of fluid from the second volume 114 to the first volume 112. The check valve 120 may be a ball valve, diaphragm valve, disc valve or the like which enables one way fluid transfer through the TFC membrane 105. In operation, fluid passage through the check valve 120 from the first volume 112 to the second volume 114 is achieved upon sufficient application of force above the cracking pressure of the check valve 120. In other words, when a pressure within the first volume 112 is greater than a cracking pressure of the check valve 120, the check valve 120 opens and fluid from the first volume 112 passes through the check valve 120 to the second volume 114. Pressure utilized to move the fluid through the check valve 120 may be generated by a user squeezing the cold pack 100 or by utilization of a mechanical compression apparatus, among other pressure generation methods. For example, the check valve may have a cracking pressure selected to be just below the vapor pressure of the solvent at a target temperature so the check valve can open upon heating the solvent.

The chamber defined by the body 101 of the cold pack 100 is separated, as described above, by the TFC membrane 105 into the first volume 112 and the second volume 114. The first volume 112 contains a solvent 116 and the second volume 114 contains a solute 118. When the solvent 116 and solute 118 are separated, the cold pack 100 does not chill or otherwise exhibit a reduction in temperature. However, when the solvent 116 passes through the check valve 120 and is allowed to contact the solute 118, an endothermic process ensues and the chilling effect of the cold pack 100 is realized.

In one embodiment, the solvent 116 is water. In another embodiment, the solvent 116 is an alcohol, such as ethanol or methanol. In another embodiment, the solvent 116 is a combination of water and alcohol. The solvent 116 is provided in an amount sufficient to supersaturate the solute 118 when the solvent 116 and solute 118 are mixed together. The solute 118 is selected to endothermically react with, or dissolve in, the solvent 116. In one embodiment, the solute 118 is ammonium nitrate, calcium ammonium nitrate, potassium nitrate, urea, or combinations and mixtures thereof. Upon mixture of the solvent 116 and solute 118, it is contemplated that the cold pack 100 may obtain temperatures as low as about 35° F. for 10-15 minutes.

After the endothermic process of the solvent 116 and the solute 118 has ceased, the resulting solution present in the second volume 114 can be separated by the TFC membrane 105. Because the TFC membrane 105 is impermeable or relatively impermeable to the solute 118 and permeable to the solvent 116, the solvent 116 can pass through the TFC membrane to the first volume 112 while the solute 118 remains in the second volume 114. Pressure applied to the second volume 114 causes the solvent 116 to pass through the TFC membrane 105. In one embodiment, the pressure applied to pass the solvent through the TFC membrane 105 may be greater than about 30 pounds per square inch (PSI), such as about 40 PSI.

While the solute 118 may not be completely dried after passage of the solvent 116 from the second volume 114 to the first volume 112 through the TFC membrane 105, it is contemplated that adequate separation of the solute 118 and solvent 116 is achieved to enable subsequent reuse of the cold pack 100. In addition, multiple TFC membranes may be utilized to increase the salt rejection rate. For example, a first TFC membrane and a second TFC membrane may be utilized to further prevent passage of solute ions to the first volume 112 containing the solvent 116 during solvent transfer across the plurality of TFC membranes. Removal of solvent from the solution in the second volume 114 raises the concentration of solute in the solution beyond the solubility limit, resulting in precipitation of at least some of the solute from the solution. The resulting precipitated solute may subsequently be exposed to solvent (as described above) sufficient to re-engage the solute and lower the temperature.

Figure 2:
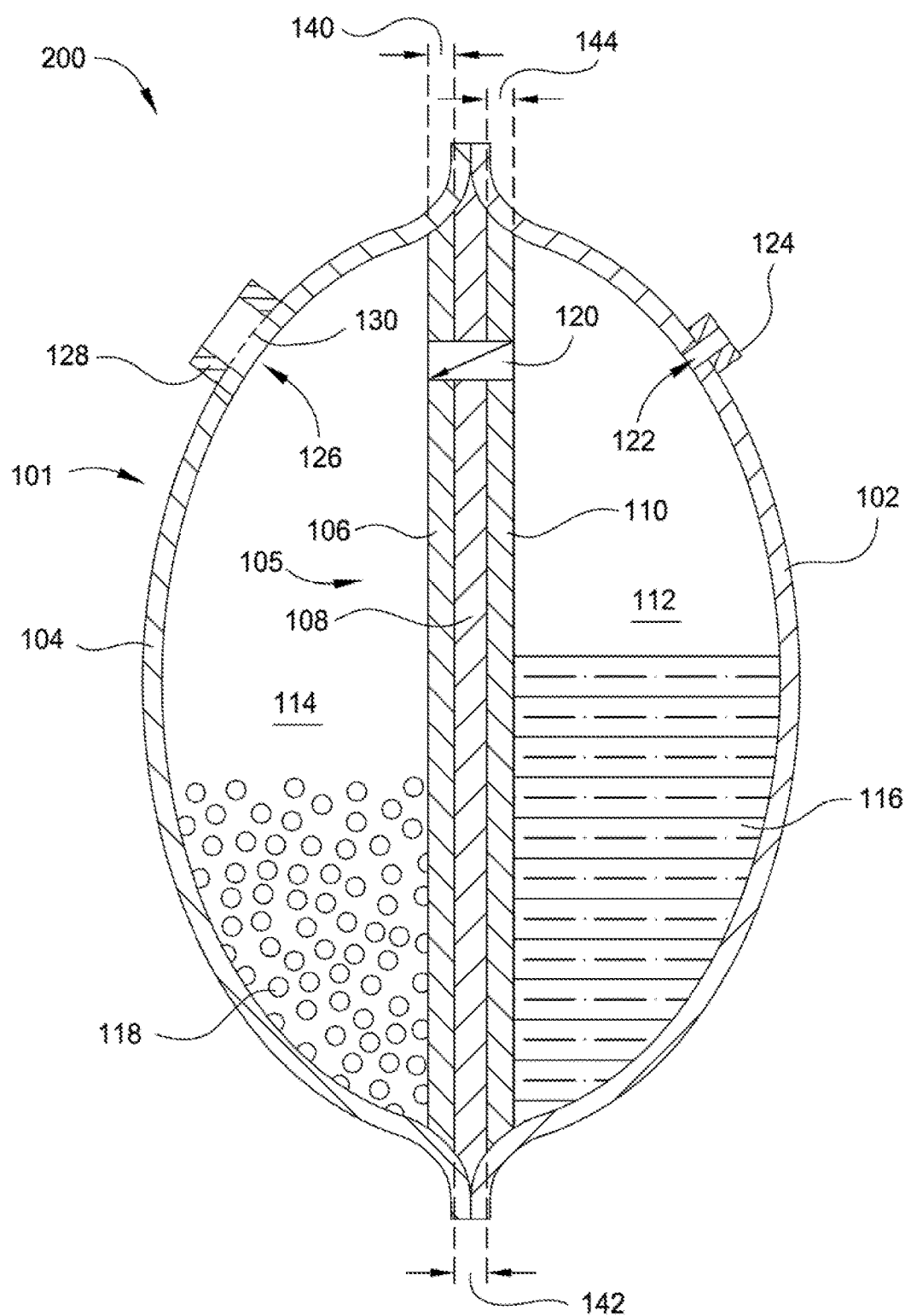
FIG. 2 illustrates a schematic, cross-sectional view of a cold pack according to one embodiment described herein.

FIG. 2 illustrates a schematic, cross-sectional view of a cold pack 200 according to one embodiment described herein. The general structure of the cold pack 200 is similar to the cold pack 100, however, a first port member 122 is disposed through the first body member 102 and a second port member 126 is disposed through the second body member 104. The first port member 122 is a tube disposed in the first body member 102. A first cap 124 may be threadably coupled to the first port member 122. The first cap 124 may be removed and additional solvent may be added to the first volume 112 through the first port member 122. Thus, should more solvent be desired to ensure supersaturation of the solute, more solvent can be added to the first volume 112 and the first cap 124 may be replaced to seal the first volume 112.

The second port member 126 is a tube disposed in the second body member 104. A second cap 128 may be threadably coupled to the second port member 126. In one embodiment, the second cap 128 may be removed and additional solute may be added to the second volume 114 through the second port member 126 should additional solute be desirable to extend the useful life of the cold pack 200. In another embodiment, a microporous membrane 130 is disposed within the second port member 126. The microporous membrane 130 is selected to enable passage of solvent vapor therethrough to further dry the solute 118. For example, the cold pack 200 may be heated by sunlight or the like and solvent vapor can be removed from the second volume 114 via the second port member 126 while solute 118 is rejected, resulting in drying of the solute to improve the reaction kinetics for subsequent utilization of the cold pack 200.

While the foregoing is directed to embodiments of the present disclosure, other and further embodiments of the disclosure may be devised without departing from the basic scope thereof, and the scope thereof is determined by the claims that follow.

What is claimed is:

1. A cold pack apparatus, comprising:
a body defining a chamber;
a thin film composite membrane coupled to the body and together with the body defining a first volume and a second volume of the chamber, wherein the thin film composite membrane comprises:
a fabric material sheet;
a thermoplastic polymer material sheet coupled to the fabric material sheet; and
a polyamide material sheet coupled to the thermoplastic polymer material sheet; and
a check valve disposed within the thin film composite membrane, the check valve in fluid communication with the first volume and the second volume.

2. The apparatus of claim 1, wherein the first volume contains a solvent.

3. The apparatus of claim 2, wherein the solvent is selected from the group consisting of water, ethanol, and methanol.

4. The apparatus of claim 1, wherein the second volume contains a solute.

5. The apparatus of claim 4, wherein the solute is selected from the group consisting of ammonium nitrate, calcium ammonium nitrate, potassium nitrate, and urea.

6. The apparatus of claim 1, wherein the fabric material sheet is a non-woven fabric material.

7. The apparatus of claim 1, wherein the fabric material sheet has a thickness of between about 50 µm and about 200 µm.

8. The apparatus of claim 1, wherein the thermoplastic polymer material sheet is a polysulfone material or a polyethersulfone material.

9. The apparatus of claim 1, wherein a thickness of the thermoplastic polymer material sheet is between about 20 µm and about 80 µm.

10. The apparatus of claim 1, wherein the polyamide material sheet has a thickness of less than about 200 nm.

11. The apparatus of claim 1, wherein the polyamide material sheet is disposed adjacent the first volume and the fabric material sheet is disposed adjacent the second volume.

12. A cold pack apparatus, comprising:
a body defining a chamber therein;
a fabric sheet coupled to the body to define a first volume and a second volume within the chamber;
a thermoplastic polymer sheet coupled to the fabric sheet and the body;
a polyamide sheet coupled to the thermoplastic polymer sheet and the body; and
a check valve disposed through the fabric sheet, the thermoplastic polymer sheet, and the polyamide sheet, wherein the check valve is operable to establish fluid communication between the first volume and the second volume.

13. The apparatus of claim 12, wherein the first volume contains a solvent.

14. The apparatus of claim 13, wherein the solvent is selected from the group consisting of water, ethanol, and methanol.

15. The apparatus of claim 12, wherein the second volume contains a solute.

16. The apparatus of claim 15, wherein the solute is selected from the group consisting of ammonium nitrate, calcium ammonium nitrate, potassium nitrate, and urea.

17. The apparatus of claim 12, wherein the check valve is a one-way check valve which is adapted to enable fluid flow from the first volume to the second volume.

18. A cold pack apparatus, comprising:
a body defining a chamber therein;
a thin film composite membrane coupled to the body and together with the body defining a first volume and a second volume of the chamber;
a check valve disposed within the thin film composite membrane, the check valve in fluid communication with the first volume and the second volume;
a fluid inlet port disposed in the body in fluid communication with the first volume; and
a fluid outlet port disposed in the body in fluid communication with the second volume.

19. The apparatus of claim 18, wherein the first volume contains a solvent and the second volume contains a solute.

* * * * *